United States Patent
Magnus et al.

(10) Patent No.: US 6,306,910 B1
(45) Date of Patent: Oct. 23, 2001

(54) USE OF GABA-ANALOGUES FOR TREATING INSOMNIA

(75) Inventors: Leslie Magnus, Livingston; Catherine A. Segal, Chester, both of NJ (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/743,370

(22) PCT Filed: Jul. 1, 1999

(86) PCT No.: PCT/US99/15058

§ 371 Date: Jan. 9, 2001

§ 102(e) Date: Jan. 9, 2001

(87) PCT Pub. No.: WO00/02546

PCT Pub. Date: Jan. 20, 2000

Related U.S. Application Data

(60) Provisional application No. 60/092,166, filed on Jul. 9, 1998.

(51) Int. Cl.[7] .................................................. A61K 31/197
(52) U.S. Cl. .......................................... 514/561; 514/567
(58) Field of Search ..................................... 514/561, 567

(56) References Cited

U.S. PATENT DOCUMENTS 5,510,381   4/1996   Pande ................................... 514/561

OTHER PUBLICATIONS

Rodenbeck et al., Somnologie, 2/1 (26–31) (abstract), 1998.*

Rao et al., "Gabapentin augments whole blood serotonin in healthy young men", abstract *J. Neural Transmission*, vol. 73, No. 2, 1988, pp. 129–134.

Placidi et al., "Effect of chronic treatment with Gabapentin on nocturnal sleep in epilepsy", American Epilepsy Society, Annual Meeting, Boston, Dec. 4–7, 1997, abstract.

Karam–Hage and Brower, "Gabapentin is helpful for insomnia in alcohol–dependent patients during early recovery", *Alcoholism Clinical and Experimental Research*, vol. 23, No. 5, Suppl., May 1999, p. 81A, abstract.

Field et al., "Gabapentin (neurontin) and S–(+)–3–isobutyl–gaba represent a novel class of selective antihyperalgesic agents", *British Journal of Pharmacology*, vol. 121, No. 8, 1997, pp. 1513–1522.

* cited by examiner

*Primary Examiner*—Phyllis G. Spivack
(74) *Attorney, Agent, or Firm*—Charles W. Ashbrook

(57) ABSTRACT

The instant invention is a method of using analogs of glutamic acid and gamma-aminobutyric acid to treat insomnia.

4 Claims, No Drawings

USE OF GABA-ANALOGUES FOR TREATING INSOMNIA

This application of a 371 of PCT/US 99/15058, filed Jul. 1, 1999, which claims the benefit of No. 60/092,166 filed Jul. 9, 1998.

BACKGROUND OF THE INVENTION

1. Field of The Invention

The present invention relates to the use of analogs of glutamic acid and gamma-aminobutyric acid (GABA) for the treatment of insomnia.

2. Description of Related Art

GABA analogs are known agents useful in antiseizure therapy for central nervous system disorders such as epilepsy, Huntington's chorea, cerebral ischemia, Parkinson's disease, tardive dyskinesia, and spasticity. It has also been suggested that the compounds can be used as antidepressants, anxiolytics, and antipsychotics. See WO 92/09560 (U.S. Ser. No. 618,692 filed Nov. 27, 1990) and WP 93/23383 (U.S. Ser. No. 886,080 filed May 20, 1992).

WO 97/33858 teaches that compounds related to gabapentin are useful or treating epilespy, faintness attacks, hypokinesia, cranial disorders, neurodegenerative disorders, depression, anxiety, panic, pain, and neuropathological disorders. WO 97/33858 does not specify what forms of pain are treated.

Additionally, the compounds of the invention are known for treatment of neuropathic pain. For example, see Rosner H; Rubin L; Kestenbaum A., Gabapentin adjunctive therapy in neuropathic pain states. Clin J Pain, 1996 March, 12:1, 56–8; Segal A Z; Rordorf G., Gabapentin as a novel treatment for postherpetic neuralgia. Neurology, 1996 April, 46:4, 1175–6; Wetzel C H; Connelly J F., Use of gabapentin in pain management. Ann Pharmacother, 1997 September 31:9, 1082–3; Zapp J J., Postpoliomyelitis pain treated with gabapentin [letter]. Am Fam Physician, 1996 June, 53:8, 2442, 2445; Cheville A, et al., Neuropathic pain in radiation myelopathy: a case report. Program book, American Pain Society (14th Annual Scientific Meeting). Abstract #95823, p. A-115; Sist T; Filadora V; Miner M; Lema M., Gabapentin for idiopathic trigeminal neuralgia: report of two cases. Neurology, 1997 May 48:5, 1467; Waldman S D, Tutorial 28: Evaluation and Treatment of Trigeminal Neuralgia. Pain Digest (1997) 7:21–24; Mellick L B; Mellick G A., Successful treatment of reflex sympathetic dystrophy with gabapentin [letter]. Am J Emerg Med, 1995 January, 13:1, 96; Mellick G A; Seng M I., The use of gabapentin in the treatment of reflex sympathetic dystrophy and a phobic disorder. Am J Pain Manage 1995; 5:7–9; Mellick G A; Mellicy L B; Mellick L B., Gabapentin in the management of reflex sympathetic dystrophy [letter]. J Pain Symptom Manage, 1995 May, 10:4, 265–6; Mellick G A; Mellick L B., Reflex sympathetic dystrophy treated with gabapentin. Arch Phys Med Rehabil, 1997 January, 78:1, 98–105 and Mackin G A., Medical and pharmacologic management of upper extremity neuropathic pain syndromes. J Hand Ther, 1997 April–June, 10:2, 96–109.

Insomnia and sleeplessness are common problems. Often, the insomnia or sleeplessness is precipitated by stress, emotional and physical causes.

U.S. Pat. No. 5,510,381, directed to the use of gabapentin to treat mania, mentions one study in which gabapentin has also been found to enhance delta-wave (deep) sleep. This effect is beneficial in acute mania and also leads to reducing the risk for onset of a new episode of mania.

SUMMARY OF THE INVENTION

This invention provides a method for treating insomnia in a mammal comprising administering to a subject suffering from insomnia an effective amount of a GABA analog. A preferred embodiment utilizes a cyclic amino acid compound of Formula I

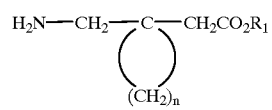

I wherein $R_1$ is hydrogen or lower alkyl and n is an integer of from 4 to 6, and the pharmaceutically acceptable salts thereof. An especially preferred embodiment utilizes a compound of Formula I where $R_1$ is hydrogen and n is 4, which compound is 1-(aminomethyl)-cyclohexane acetic acid, known generically as gabapentin.

In another embodiment, the invention includes treating insomnia with a compound of Formula II.

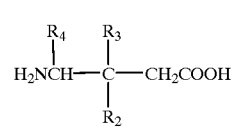

II wherein $R_2$ is a straight or branched alkyl of from 1 to 6 carbon atoms, phenyl, or cycloalkyl having from 3 to 6 carbon atoms; $R_3$ is hydrogen or methyl; and R4 is hydrogen, methyl, or carboxyl; or an individual enantiomeric isomer thereof; or a pharmaceutically acceptable salt thereof, in unit dosage form, to a mammal in need of said treatment.

Preferred compounds of the invention are those wherein $R_4$ and $R_3$ are hydrogen, and $R_2$ is —$(CH_2)_{0-2}$-i $C_4H_9$ as an (R), (S), or (R,S) isomer.

The more preferred compounds of Formula II invention are (S)-3-(aminomethyl)-5-methylhexanoic acid and 3-aminomethyl-5-methyl-hexanoic acid, now known generically as pregabalin.

DETAILED DESCRIPTION OF THE PREFERRED EMBODIMENTS

The method of this invention utilizes any GABA analog. A GABA analog is any compound derived from or based upon gamma-aminobutyric acid. The compounds are readily available, either commercially, or by synthetic methodology well-known to those skilled in the art of organic chemistry. The preferred GABA analogs to be utilized in the method of this invention are cyclic amino acids of Formula I. These are described in U.S. Pat. No. 4,024,175, which is incorporated herein by reference. Another preferred method utilizes the GABA analogs of Formula II, and these are described in U.S. Pat. No. 5,563,175 which is incorporated herein by reference.

All that is required to practice the method of this invention is to administer a GABA analog in an amount that is effective to treat insomnia. Such amounts will generally be from about 1 to about 300 mg per kg of subject body weight. Typical doses will be from about 10 to about 5000 mg per day for an adult subject of normal weight. It is expected that common doses that might be administered could be from 100 mg three times a day up to 600 mg four times a day.

Commercially available capsules of 100 mg, 300 mg, and 400 mg of gabapentin can be administered. Alternate forms include liquids and film-coated tablets.

If a compound of Formula II, such as pregabalin is used, the dosage level is one sixth that of gabapentin. The dosage range for pregabalin is from about 0.15 mg to about 50 mg per kg per day of subject body weight. Typical dosages for pregabalin will be from about 1.6 mg to about 840 mg per day with individual dosages ranging from abut 0.15 mg to about 65 mg per dose.

The compounds used in the present invention may form pharmaceutically acceptable salts with both organic and inorganic acids or bases. For example, the acid addition salts of the basic compounds are prepared either by dissolving the free base in aqueous or aqueous alcohol solution or other suitable solvents containing the appropriate acid and isolating the salt by evaporating the solution. Examples of pharmaceutically acceptable salts are hydrochlorides, hydrobromides, hydrosulfates, etc. as well as sodium, potassium, and magnesium, etc. salts.

The compounds of the Formula II can contain one or several asymmetric carbon atoms. The invention includes the individual diastereomers or enantiomers, and the mixtures thereof. The individual diastereomers or enantiomers may be prepared or isolated by methods already well-known in the art.

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol, glycerin; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredients in the foregoing compositions can be varied within wide limits, but for practical purposes it is preferably present in a concentration of at least 10% in a solid composition and at least 2% in a primary liquid composition. The most satisfactory compositions are those in which a much higher proportion of the active ingredient is present.

Routes of administration of the subject compound or its salts are oral or parenteral. For example, a useful intravenous dose is between 5 and 50 mg and a useful oral dosage is between 20 and 800 mg. The dosage is within the dosing range used in treatment of pain or as would be with the needs of the patient as described by the physician.

The benefit of using GABA analogs to treat insomnia is that they are not addictive. Additionally, GABA analogs have a half-life in the body that is suitable to work during the evening and subsequently clear the body by morning to allow for easy arousal. GAGA analog's, particularly gabapentin's, method of action is different from other sleep enchancing agents. The GABA analogs can be combined with other agents to enhance the sleep inducing effects. Such agents include melatonin, trytophan, valerian, passiflora, antihistamines, such as diphenydramine hydrochloride or doxylamine succinate, densokiazepene and non-benzodipend hypnotics.

Additional advantages of using the compounds of Formula I and II, especially gabapentin and pregabalin, in the present invention include the relatively nontoxic nature of the compounds, the ease of preparation, the fact that the compounds are well-tolerated, and the ease of IV administration of the drugs. Gabapentin has few interactions with major classes of drugs since it is not metabolized in the liver, but rather excreted unchanged from the body. Further, the drugs are not metabolized in the body. The subjects treated with the method of the present invention are mammals, including humans.

The GABA analogs used in the method of the present invention are not addictive. This is a significant advantage over other sleep aids. Also, these compounds have a half life that is suitable to work during the evening and subsequently clear the body by morning to allow for easy arousal. The method of action of the GABA analogs is different than other hypnotics and thus can be combined with them to enhance the sleep inducing effects. These agents could include melatonin, trytophan, valerian, passiflora, classical antihistamines such as diphenhydramine hydrochloride or doxylamine succinate, as well as benzodiazepene and non-benzodiazepene hypnotics.

What is claimed is:

1. A method for treating a mammal suffering from insomnia comprising administering an effective amount of a compound according to formula II:

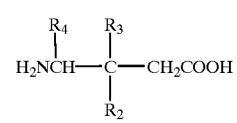

wherein $R_2$ is a straight or branched alkyl of from 1 to 6 carbon atoms, phenyl or cycloalkyl having from 3 to 6 carbon atoms, $R_3$ is hydrogen or methyl; and $R_4$ is hydrogen, methyl, or carboxyl.

2. The method according to claim 1, wherein Formula II comprises pregabalin.

3. The method according to claim 2, comprising from about 0.15 mg to about 65 mg of pregabalin.

4. The method according to claim 1, comprising from about 0.15 mg to about 65 mg of Formula II.

* * * * *